(12) United States Patent
Sung et al.

(10) Patent No.: US 6,818,442 B2
(45) Date of Patent: Nov. 16, 2004

(54) AIDS DNA VACCINE THAT PREVENTS SIVMAC239 VIRUS INFECTION IN MONKEYS

(75) Inventors: Young Chul Sung, Kyung-buk (KR); You Suk Suh, Kyung-buk (KR)

(73) Assignees: Genexine Co. Ltd., Seoul (KR); Pohang University of Science and Technology, Pohang (KR)

(*) Notice: Subject to any disclaimer, the term of this patent is extended or adjusted under 35 U.S.C. 154(b) by 57 days.

(21) Appl. No.: 09/730,716

(22) Filed: Dec. 6, 2000

(65) Prior Publication Data

US 2001/0004531 A1 Jun. 21, 2001

(30) Foreign Application Priority Data

Dec. 6, 1999 (KR) .......................................... 1999-55129

(51) Int. Cl.$^7$ .......................... C12N 5/00; C12N 15/00; A01N 43/04; A01N 63/00
(52) U.S. Cl. ..................... 435/320.1; 435/325; 435/455; 514/44; 424/93.2; 424/93.6; 424/184.1; 424/188.1
(58) Field of Search .............................. 435/69.1, 320.1, 435/325, 455; 514/44; 424/93.1, 93.2, 93.6, 184.1, 188.1

(56) References Cited

U.S. PATENT DOCUMENTS

| | | | | |
|---|---|---|---|---|
| 5,981,505 A | * | 11/1999 | Weiner et al. | 514/44 |
| 5,994,136 A | * | 11/1999 | Naldini et al. | 435/455 |
| 6,479,281 B1 | * | 11/2002 | Gottlinger et al. | 435/320.1 |

OTHER PUBLICATIONS

Daniel, M. D, et al. "Protective Effects of a Live Attenuated SIV Vaccine with a Deletion in the net Gene" (1992) Science vol. 258, pp. 1938–1941.*

Smith, J. M. et al. "Preparation and Induction of Immune Responses by a DNA AIDS Vaccine" (2000) Viral Immunol vol. 13, No. 3, pp. 343–351.*

Hanke, T. et al. "Effective Induction of Simian Immunodeficiency Virus–Specific Cytotoxic T Lymphocytes in Macaques by Using a Multiepitope Gene and DNA Prime–Modified Vaccinia Virus Ankara Boost Vaccination Regimen" (1999) J Virol vol. 73, No. 9, pp. 7524.*

Morris–Vasios, C. et al. "Avian Sarcoma–Leukosis Virus pol–endo Proteins Expressed Independently in Mammalian Cells Accumulate in the Nucleus but Can Be Directed to Other Cellular compartments" (1998) J Virol vol. 62, No. 1, pp. 349–353.*

Hazama, M. et al. "Adjuvant–independent Enhanced Immune Responses to Recombinant Herpes Simplex Virus Type 1 Glycoprotein D by Fusion with Biologically Active Interleukin–2" (1993) Vaccine vol. 11, No. 6, pp. 629–636.*

A.H. Lee et al., "DNA inoculations with HIV–1 recombinant . . . responses," Vaccine, 1999, 17:473–479.

S. Lu et al., "Simian Immunodeficiency . . . Macaques," Journal of Virology, Jun. 1996, 70(6):3978–3991.

* cited by examiner

*Primary Examiner*—Jeffrey Fredman
*Assistant Examiner*—Sumesh Kaushal
(74) *Attorney, Agent, or Firm*—Gates & Cooper LLP

(57) ABSTRACT

The present invention relates to a plasmid carrying simian immunodeficiency virus (SIV)-derived genes. Particularly, the present invention relates to the plasmid pSIV/GE which carrys gag, protease, env and rev gene, all derived from SIV, but not tat and nef gene and the plasmid pSIV/pol which carrys SIV-derived pol gene; the plasmid pHIV/GE and pHIV/pol that are substituted the SIV-derived genes in the plasmid pSIV/GE and pSIV/pol by human immunodeficiency virus (HIV)-derived corresponding genes; DNA vaccine containing the plasmid pSIV/GE and pSIV/pol; and DNA vaccine containing the plasmid pHIV/GE and pHIV/pol. The present invention offers AIDS DNA vaccines which successfully exert perfect medicinal efficacy on primates, giving a measure of success in developing effective AIDS DNA vaccines applicable to humans. The plasmid of the present invention can be effectively used for not only AIDS prevention by AIDS infection but also therapeutic agent for AIDS.

1 Claim, 10 Drawing Sheets

Figure 3:
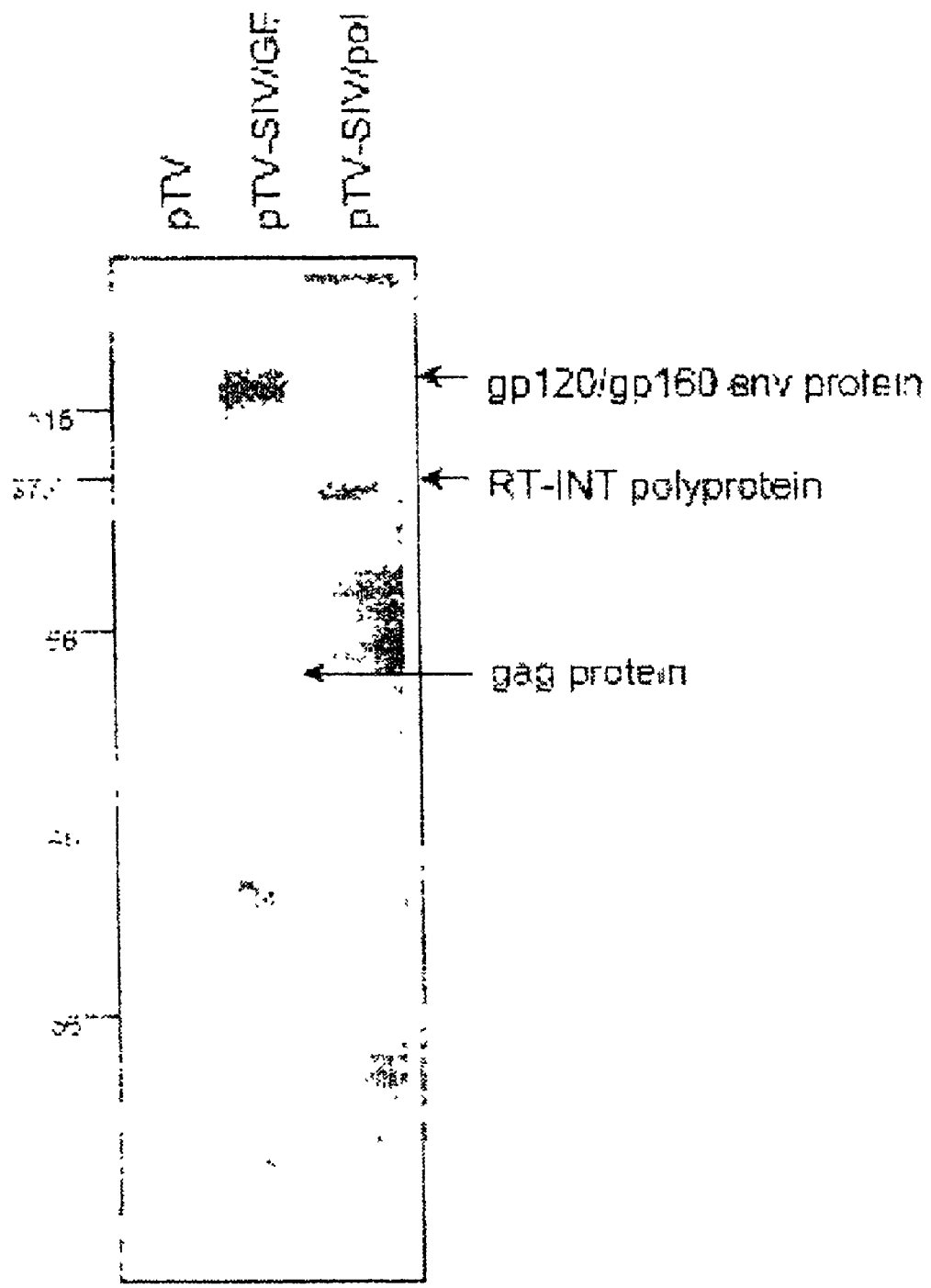

FIG. 1
SIVmac239
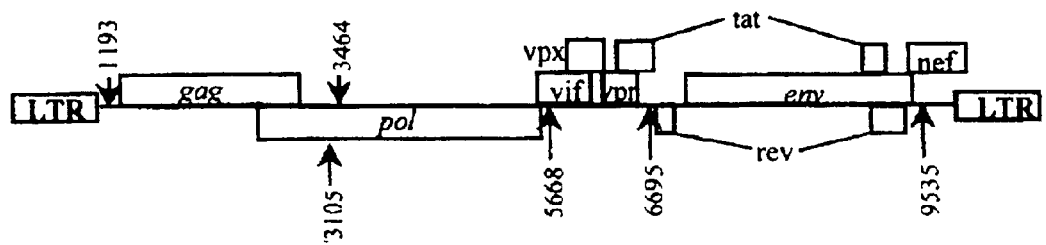
SIV/GE (5.1 kb)
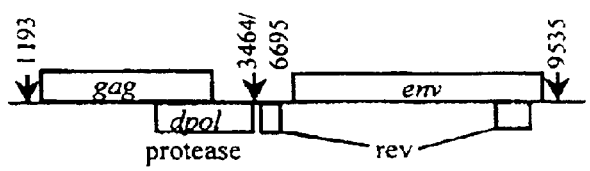
SIV/pol (2.7kb)
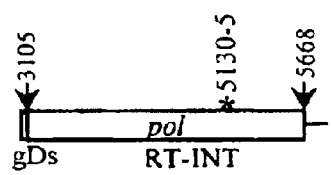
SIV/GE-GC (6.2 kb)
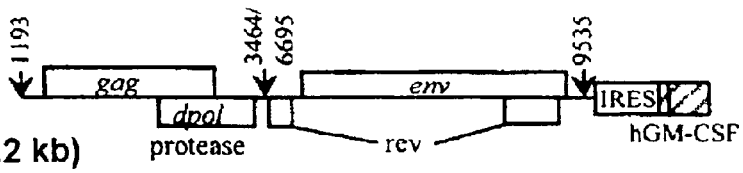
SIV/pol-IL-2 (3.7kb)
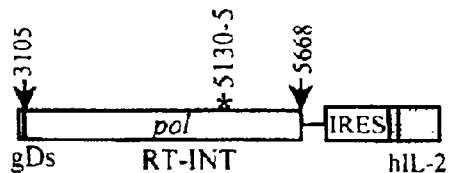

FIG. 2
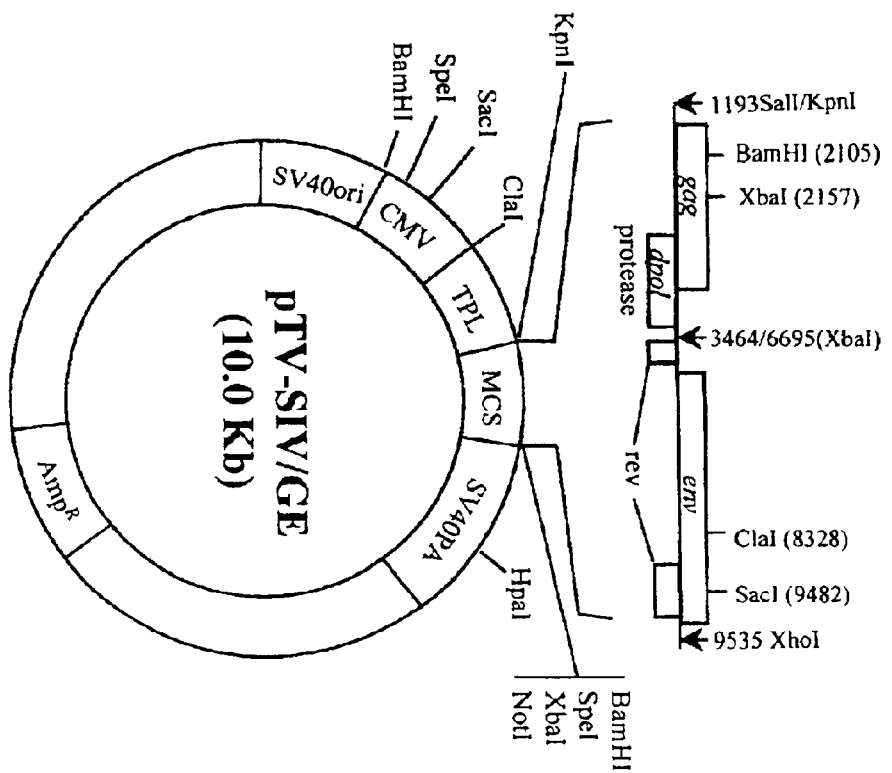
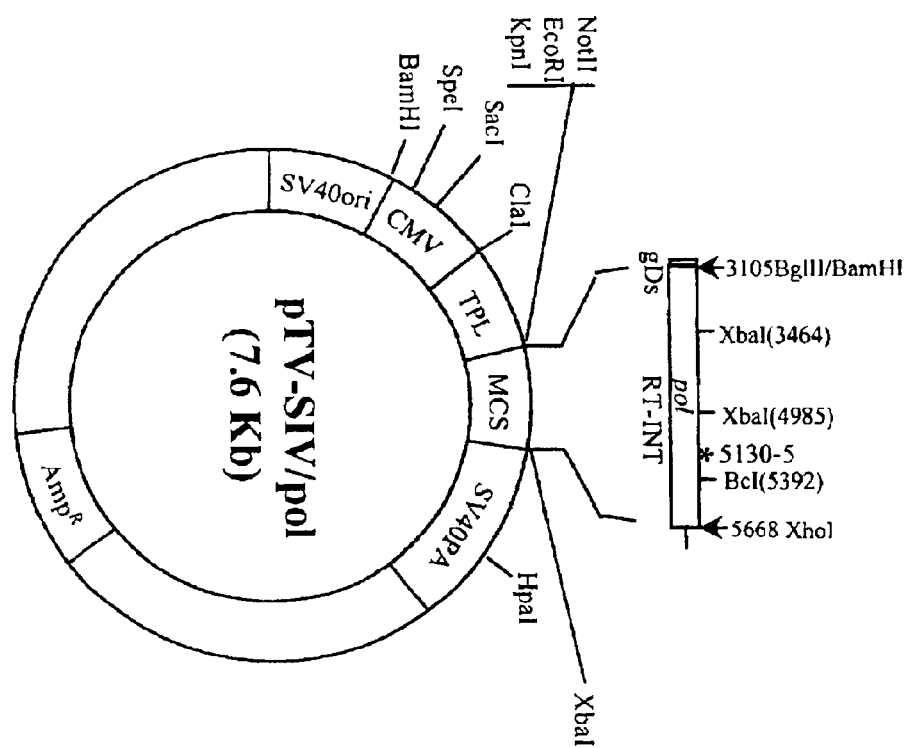

Weeks after SIVmac239 challenge

Weeks after SIVmac239 challenge

FIG. 8

| Monkey# | group | Cell-associated viral load (# of infectious cells per 1 x 10⁶ mononuclear cells) | | | | | | | | | | | |
|---|---|---|---|---|---|---|---|---|---|---|---|---|---|
| | | PBMC | LN-cervicalis | Palatine tonsil | Lingual tonsil | spleen | LN-axillaris | LN-inguinal | LN-mesent. | LN-submandib. | thymus | LN-retro-pharyng. | Peyer's patches |
| *Week 25 post-infection* | | | | | | | | | | | | | |
| 8777 | 2 | * | ND[b] | ND | ND | ND | ND | 8 | ND | ND | ND | ND | ND |
| 8780 | 2 | — | ND | ND | ND | ND | ND | 16 | ND | ND | ND | ND | ND |
| *Week 52 post-infection* | | | | | | | | | | | | | |
| 8777 | 2 | — | ND | ND | ND | ND | — | ND | ND | ND | ND | ND | ND |
| 8780 | 2 | 0.33 | ND | ND | ND | ND | 1 | ND | ND | ND | ND | ND | ND |
| 8783 | 3 | 1024 | ND | ND | ND | ND | 1024 | ND | ND | ND | ND. | ND | ND |
| *Week 60 post-infection (necropsy)* | | | | | | | | | | | | | |
| 8777 | 2 | — | — | ND | ND | — | — | ND | — | — | — | — | — |
| 8780 | 2 | 1 | — | — | — | 16 | — | ND | 4 | 2 | — | 4 | — |

FIG. 9

| Group (monkey#) | Immunogen (weeks post the 1st immunization) | | | | | Challenge (46 weeks) |
|---|---|---|---|---|---|---|
| | 1'DNA (0week) | 2'DNA (8 weeks) | 3'DNA or protein (17weeks) | 4'DNA or protein (25 weeks) | 5'DNA or protein (44 weeks) | |
| 1 (8645, 8772, 8774) | pTV: 800ug | ↙ | ↙ | ↙ | ↙ | SIVmac239 dose: 10 MID$_{50}$ route: i.v |
| 2 (8777, 8780) | pTV-GE: 400ug pTV-dpol: 400ug | ↙ | ↙ | ↙ | ↙ | |
| 3 (8783, 8786, 8787) | pTV-GE: 200ug pTV-GE-GC: 200ug pTV-dpol: 200ug pTV-dpol-IL2: 200ug | ↙ | | ↙ | | |
| 4 (8789, 8791, 8792) | pTV-GE: 400ug pTV-dpol: 400ug | ↙ | rRT: 50ug gp120: 50ug p27: 50ug with alum | | rRT: 50ug gp120: 50ug p27: 50ug with alum adjuvant | |

SEQUENCE LISTING

```
<160> NUMBER OF SEQ ID NOS:  12

<210> SEQ ID NO 1
<211> LENGTH: 20
<212> TYPE: DNA
<213> ORGANISM: Artificial Sequence
<220> FEATURE:
<223> OTHER INFORMATION: 1193Kpn, a synthetic oligonucleotide primer

<400> SEQUENCE: 1
cgggtcggta ccagacggcg                                                   20

<210> SEQ ID NO 2
<211> LENGTH: 22
<212> TYPE: DNA
<213> ORGANISM: Artificial Sequence
<220> FEATURE:
<223> OTHER INFORMATION: 3464Xba, a synthetic oligonucleotide primer

<400> SEQUENCE: 2
atctagaggt atggagaaat at                                                22

<210> SEQ ID NO 3
<211> LENGTH: 20
<212> TYPE: DNA
<213> ORGANISM: Artificial Sequence
<220> FEATURE:
<223> OTHER INFORMATION: 6695Xba, a synthetic oligonucleotide primer

<400> SEQUENCE: 3
gccctctaga agcatgctat                                                   20

<210> SEQ ID NO 4
<211> LENGTH: 32
<212> TYPE: DNA
<213> ORGANISM: Artificial Sequence
<220> FEATURE:
<223> OTHER INFORMATION: 9641NotI, a synthetic oligonucleotide primer

<400> SEQUENCE: 4
```
ggaagcggcc gcctcactga taccoctacc aa                                32

<210> SEQ ID NO 5
<211> LENGTH: 20
<212> TYPE: DNA
<213> ORGANISM: Artificial Sequence
<220> FEATURE:
<223> OTHER INFORMATION: 8328Cla, a synthetic oligonucleotide primer

<400> SEQUENCE: 5
actgtatcga ttggaattgg                                              20

<210> SEQ ID NO 6
<211> LENGTH: 30
<212> TYPE: DNA
<213> ORGANISM: Artificial Sequence
<220> FEATURE:
<223> OTHER INFORMATION: 9535Xho, a synthetic oligonucleotide primer

<400> SEQUENCE: 6
ctccctcgag tattcatata ctgtccctga                                   30

<210> SEQ ID NO 7
<211> LENGTH: 24
<212> TYPE: DNA
<213> ORGANISM: Artificial Sequence
<220> FEATURE:
<223> OTHER INFORMATION: BamHI-tag primer

<400> SEQUENCE: 7
aatggatcca tagctaaagt agag                                         24

<210> SEQ ID NO 8
<211> LENGTH: 25
<212> TYPE: DNA
<213> ORGANISM: Artificial Sequence
<220> FEATURE:
<223> OTHER INFORMATION: XhoI-tag primer

<400> SEQUENCE: 8
atttctcgag gctatgccac ctctc                                        25

<210> SEQ ID NO 9
<211> LENGTH: 24
<212> TYPE: DNA
<213> ORGANISM: Artificial Sequence
<220> FEATURE:
<223> OTHER INFORMATION: a PCR primer for the mutagenesis of pol gene

<400> SEQUENCE: 9
agtggtgcta actttgcttc gcaa                                         24

<210> SEQ ID NO 10
<211> LENGTH: 23
<212> TYPE: DNA
<213> ORGANISM: Artificial Sequence
<220> FEATURE:
<223> OTHER INFORMATION: a PCR primer for the mutagenesis of pol gene

<400> SEQUENCE: 10
tgtgtgtaga tgtgtaatag gcc                                          23

<210> SEQ ID NO 11
<211> LENGTH: 30
<212> TYPE: DNA
<213> ORGANISM: Artificial Sequence -continued

```
<220> FEATURE:
<223> OTHER INFORMATION: hGM-CSF specific primer (forward)

<400> SEQUENCE: 11
tggaccatgg ggctgcagag cctgctgctc                                    30

<210> SEQ ID NO 12
<211> LENGTH: 30
<212> TYPE: DNA
<213> ORGANISM: Artificial Sequence
<220> FEATURE:
<223> OTHER INFORMATION: hGM-CSF specific primer (reverse)

<400> SEQUENCE: 12
tgggaattct cactcctgga ctggctccca                                    30
```

AIDS DNA VACCINE THAT PREVENTS SIVMAC239 VIRUS INFECTION IN MONKEYS

FIELD OF THE INVENTION

The present invention relates to a plasmid containing simian immunodeficiency virus (hereinafter referred to as "SIV")-derived genes.

Particularly, the present invention relates to the plasmid pSIV/GE which contains gag, protease, env and rev gene, all derived from SIV, but not tat and nef gene and the plasmid pSIV/pol which contains SIV-derived pol gene; the plasmid pHIV/GE and pHIV/pol that are substituted the SIV-derived genes in the plasmid pSIV/GE and pSIV/pol by human immunodeficiency virus (hereinafter referred to as "HIV")-derived corresponding genes; AIDS DNA vaccine containing the plasmid pSIV/GE and pSIV/pol; and AIDS DNA vaccine containing the plasmid pHIV/GE and pHIV/pol.

BACKGROUND

It has been found that plasmid DNA, when injected into mice without being associated with any adjuvant, can generate antibody and CTL responses to viral antigens encoded by the plasmid DNA, and elicit protective immunity against viral infection (Ulmer at al., *Science*, 259:1745, 1993). Starting from this, there have been reported many research results regarding the induction of humoral and cellular immune responses resulting from the introduction of DNA vaccines containing various viral genes in animal models (Chow et al., *J. Virol.*, 71:169, 1997; McClements et al., *Proc. Natl. Acad. Sci. USA*, 93:11414, 1996; Xiang et al., *Virology*, 199:132, 1994; Wang et al., *Virology*, 211:102, 1995; Lee et al., *Vaccine*, 17:473, 1999; Lee et al., *J. Virol.*, 72:8430, 1998).

DNA vaccines are highly safe, as proven by the fact that the clinical testing of DNA vaccines on human beings was allowed by the FDA of U.S.A. only four years after great success was reported in the research using small animals. With the advantage of being able to induce potent and persistent cellular immune responses, DNA vaccines have been considered strong candidates for prevention and therapy of AIDS.

In connection to candidates for AIDS vaccines, attenuated viruses, subunit vaccines, and live virus vector vaccines have been under study. Of these candidates, attenuated viruses induce the most potent immune responses, but have the danger of being converted into virulent strains since they can replicate in the host. In fact, the infection of some attenuated viruses caused AIDS in experiments on monkeys, raising concerns about their safety.

On the other hand, subunit vaccines suffer from the problem of being unable to induce CTL immune responses necessary for protection against HIV. In the case of live virus vector vaccines, questions have been raised whether the vectors themselves may cause infection and diseases.

For vaccines against HIV to be applied to humans, their virtues must be first confirmed through testing on primates. Primate animal models for use in infection and vaccination ranging from HIV/chimpanzee model to SIVmac/rhesus monkey model, are discriminately employed in consideration of the severity of the diseases caused and the difficulty in inducing protective immune responses in them.

Particularly, rhesus monkey models are quite difficult to protect from infection by SIVmac virus and SIVmac/rhesus monkey models, that is, rhesus monkey models infected by SIVmac virus, are recognized as being the closest model to HIV-infected humans (Hanke et al., *J. Virol.*, 73:7524, 1999). SIVmac/rhesus monkey models are very similar to HIV-1 infected humans in the following aspects:

1) host immune response after infection,
2) route of infection,
3) occurrence of persistent infection,
4) disease induction in association with a decrease in $CD4^+$ cell number,
5) impossibility of preventing the infection by use of neutralizing antibodies alone, and
6) pattern of viral loads in infected host.

With these close similarities, SIVmac/rhesus monkey models, in spite of SIVmac being different from HIV in base sequence, are recognized as the most preferable animal models. AIDS DNA vaccines developed so far are reported to inhibit AIDS infection in the animal models which are most easily protected like HIV/chimpanzee models. However, chimpanzees are not the best models since AIDS does not occur in HIV-infected chimpanzees.

Another animal model, chimeric simian-human immunodeficiency virus (SHIV)/monkey model, was designed for evaluating the efficacy of envelope-based HIV-1 vaccines. At the time when SHIV was first created, it did not induce disease in monkeys, but after having undergone repeated in vivo passage, some SHIV was transformed into virulent mutants which are able to cause a fatal disease in monkeys (Reimann et al., *J. Virol.*, 70:6922, 1996). However, SHIV has the drawback of being an artificial recombinant virus which does not exist in the natural environment.

Accordingly, the SIVmac/rhesus monkey model is considered to be the most preferable in evaluating the efficacy of AIDS vaccines. According to what is known thus far, the SIVmac/rhesus monkey model was successfully protected from SIV infection only when attenuated viruses, whose safety in humans is in question, were used (Daniel et al., *Science*, 258:1938, 1992), but failed to be protected from SIV when using other types of vaccines, including DNA vaccines (Lu et al., *J. Virol.*, 70:3978, 1996). Thus, there remains an urgent need to develop a DNA vaccine capable of directing protection against SIV infection in SIVmac/rhesus monkey models.

Among plasmid DNA vaccines which have failed to induce protection in SIVmac/rhesus monkey models, thus far, there are plasmids which not only carry gag, env, and rev genes together, but also code for accessory proteins such as tat, nef, vpr, and vpx, and plasmids which anchor env genes sourced from various species (Lu, et al., *J. Virol.*, 70:3978, 1996).

In a study using a plasmid carrying an env gene of HIV and a plasmid carrying a gag/pol gene, an $HIV_{SF}$/chimpanzee model succeeded the protection (Boyer et al., *Nat. Med.*, 3:526, 1997). However, since HIV/chimpanzee model is easy to generate the protective responses by immunization, it is likely that these plasmids will not show similar immune effects, raising the question whether they can effectively function as AIDS vaccines in humans.

The AIDS vaccines used in the prior study is believed to fail to induce effective protection against SIVmac infection for the following reasons. First, based on the research report that accessory genes of HIV, such as nef and tat, inhibit and disturb immune responses in vitro (Lindemann et al., *J. Exp. Med.*, 179:797, 1994; Viscidi et al., *Science*, 246:1616, 1989), those genes, if used as immunogens, may negatively affect the induction of protective immune responses against AIDS virus in humans and monkeys. Next, effective use was not made of a pol gene, a HIV gene encoding many CTL markers (epitopes), which are known to play an important role in protective immune responses.

Thus far, the successful immune protection generated in SIVmac/rhesus monkey models was unique among attenuated viruses, whose safety in humans is in question (Daniel et al., *Science,* 258:1938, 1992). Accordingly, if any plasmid DNA vaccine successfully induces protection in SIVmac/rhesus monkey models, the plasmid DNA itself can be evaluated as an effective AIDS vaccine and thus be applied to humans.

Leading to the present invention, the intensive and thorough research on excellent protection against AIDS virus, conducted by the present inventors aiming to circumvent above problems encountered in prior arts, resulted in the finding that a plasmid carrying a combination of gag, protease, env and rev genes or a combination of genes coding for reverse transcriptase and integrase, respectively, can induce excellent protective effects in SIVmac/rhesus monkey models with great safety.

SUMMARY OF THE INVENTION

It is an object of the present invention to provide a plasmid vaccine capable of inducing protective effects in SIVmac/rhesus monkey models.

It is another object of the present invention to establish a plasmid immunogen which can be used in the prophylaxis and therapy of human AIDS caused by HIV.

In accordance with the present invention, the foregoing objects and advantages are readily obtained.

The present invention provides a plasmid carrying gag, protease, env and rev genes, all derived from SIV, but not tat and nef genes and a plasmid carrying a SIV-derived pol gene encoding for a reverse transcriptase and an integrase.

The present invention also provides plasmids in which the SIV genes are substituted by corresponding HIV-derived genes.

In addition, the present invention provides DNA vaccines comprising combinations of the plasmids carrying SIV-derived genes or the plasmids carrying HIV-derived genes.

Further features of the present invention will appear hereinafter.

BRIEF DESCRIPTION OF THE DRAWINGS

FIG. 1 shows DNA constructs of SIV-derived gene that are included plasmid pSIV/GE and pSIV/pol of the present invention in comparision with the total genome of SIV.

FIG. 2 shows restriction maps of plasmid pSIV/GE and pSIV/pol used in the present invention.

FIG. 3 shows a result of immunoblotting after plasmid pTV-SIV/GE and pTV-SIV/pol are transfected into COS-7 cell.

FIG. 4 shows cell associated viral loads in blood of challenged monkeys, wherein Group 1; pTV, Group 2; pTV-SIV/GE+pTV-SIV/pol, Group 3; pTV-SIV/GE+pTV-SIV/pol+pTV-SIV/GE-GC+pTV-SIV/pol-IL-2, Group 4; pTV-SIV/GE+pTV-SIV/pol priming and subunit vaccine boosting.

FIG. 5 shows absolute CD4+ counts in challenged monkeys, wherein

Group 1; pTV,

Group 2; pTV-SIV/GE+pTV-SIV/pol,

Group 3; pTV-SIV/GE+pTV-SIV/pol+pTV-SIV/GE-GC+pTV-SIV/pol-IL-2,

Group 4; pTV-SIV/GE+pTV-SIV/pol priming and subunit vaccine boosting.

FIG. 6 shows percentage of $CD29^{+}CD4^{+}$ cells in the peripheral blood lymphocytes of monkeys infected with SIVmac, wherein Group 1; pTV, Group 2; pTV-SIV/GE+pTV-SIV/pol, Group 3; pTV-SIV/GE+pTV-SIV/pol+pTV-SIV/GE-GC+pTV-SIV/pol-IL-2, Group 4; pTV-SIV/GE+pTV-SIV/pol priming and subunit vaccine boosting.

FIG. 7 shows postchallenge levels of p27 antigenemia, wherein

Group 1; pTV,

Group 2; pTV-SIV/GE+pTV-SIV/pol,

Group 3; pTV-SIV/GE+pTV-SIV/pol+pTV-SIV/GE-GC+pTV-SIV/pol-IL-2,

Group 4; pTV-SIV/GE+pTV-SIV/pol priming and subunit vaccine boosting.

FIG. 8 shows cell associated viral load in SIV-DNA immunized rhesus monkey at 25, 52 and 60 weeks after SIVmac 239 challenge, wherein a.–; negative, b.ND; not done.

FIG. 9 shows name and composition of AIDS DNA vaccines used in the present invention, wherein Group 1: pTV, Group 2: pTV-SIV/GE(“pTV-GE”)+pTV-SIV/pol(“pTV-dpol”), Group 3: pTV-SIV/GE(“pTV-GE”)+pTV-SIV/pol(“pTV-dpol”)+pTV-SIV/GE-GC(“pTV-GE-GC”)+pTV-SIV/pol-IL-2(“pTV-dpol-IL2”), Group 4: pTV-SIV/GE(“pTV-GE”)+pTV-SIV/pol(“pTV-dpol”) priming and subunit vaccine boosting.

FIG. 10 shows a schematic of immunization schedule for each group of monkeys.

DETAILED DESCRIPTION OF PREFERRED EMBODIMENTS

Hereinafter, the present invention is described in detail.

The present invention provides a plasmid carrying gag, protease, env and rev genes, all derived from SIV, but not tat and nef genes and a plasmid carrying a SIV-derived pol gene encoding for a reverse transcriptase and an integrase The present invention pertains to induction of excellent, protective effects in SIVmac/rhesus monkey models with a plasmid DNA vaccine. In this regard, two different plasmids are provided, 1) one carrying gag, protease, env and rev genes, but neither a tat gene nor a nef gene, and 2) the other comprising a gene coding for an SIV-derived reverse transcriptase and a pol gene coding for an integrase, which are termed "pSIV/GE" and "pSIV/pol", respectively, for convenience's sake.

With reference to FIG. 1, there are shown DNA constructs consisting of SIV-derived genes, along with SIVmac239 genome. As shown in this diagram, pSIV/GE carries a gag gene encoding a matrix protein (MA), a capsid protein (CA) and a nucleocapsid protein (NC), all derived from SIV. In addition, a protease gene is incorporated into pSIV/GE, along with a rev gene and an env gene, which code for Rev and envelope proteins, respectively. A feature of pSIV/GE is to comprise neither nef nor tat, each encoding an accessory protein.

With reference to FIG. 2, there are restriction maps of the recombinant plasmids pTV-SIV/GE and pTV-SIV/pol constructed according to embodiments of the present invention. Each of the two pTV2 vectors, into which DNA constructs, SIV/GE and SIV/pol, are respectively inserted, has an early promoter/enhancer derived from cytomegalovirus (represented by "CMV" in FIG. 2) and an adenovirus tripartite leader/intron sequence (represented by "TPL" in FIG. 2). In each vector, SV40 ORI and SV40 PA stand for a replication origin and a poly A sequence, derived from SV40, respectively. These pTV2 vectors, which are based on the vector pTX previously made by the present inventors (Lee et al., Vaccine, 17:473, 1999), have been used as DNA vaccine vectors in studies on small animals (Lee et al., J. Virol., 72:8430, 1998; Cho et al., Vaccine, 17:1136, 1999). It is obvious to those skilled in the art that various changes and modifications may be made on promoter types and glycoprotein signal sequence types and lengths, depending on purposes.

In pSIV/pol, a pol gene encoding an RT and an integrase, both derived from SIV, is anchored. Of the pol gene area responsible for the integrase, a base sequence of 5130–5135 is known to be indispensable for the enzymatic activity of the integrase. Therefore, this DNA stretch can be modified to suppress the activity of the integrase, thereby preventing the virus from replicating in host cells. Such a mutant gene further lowers the low possibility that viruses capable of replication in the vaccine after vaccination are produced, guaranteeing the safety of the DNA vaccine. The position number of the base sequence conforms to the SIVmac239 clone having a GenBank Accession Number of M33262.

In one preferable embodiment of the present invention, a signal sequence encoding 33 N-terminal amino acid residues of the glycoprotein D (gD) of herpes simplex virus (HSV) is fused to the 5'-end of the pol and subjected to the direct transcriptional control of the CMV promoter to enhance the expression frequency of the RT and integrase.

Deletion was made of the bases at positions 5130–5132 from the integrase region of the pol gene while the bases at 5133–5135 were mutated so as to express $Ser_{117}$ instead of $Asn_{117}$. As a result of various experiments, this mutant SIVmac239 virus was found to be unable to proliferate in host cells.

FIG. 1 shows a schematic diagram of a SIV-derived gene construct (SIV/pol) to be inserted to pSIV/pol. FIG. 2 shows a restriction map of the plasmid pTV-SIV/poly prepared according to a preferred embodiment of the present invention. However, it should be understood that mutation processes, promoter types, glycoprotein signal sequence types and lengths can be modified in diverse manners, depending on purposes.

Each of the plasmids pTV-SIV/GE and pTV-SIV/pol was transformed to DH5α cells and the transformed strains were deposited in the Korean Collection for Type Culture of Korea Research Institute of Bioscience and Biotechnology (KRIBB), at #52 Oun-dong, Yusong-ku, Taejon 305–333, Republic of Korea, on Nov. 27, 1999 (Accession NO; KCTC 0702BP and KCTC 0703BP).

Expression of the prepared plasmids pTV-SIV/GE and pTV-SIV/pol in in vitro cell culture systems started with the transfection into COS-7 cells (ATCC CRL-1651) by a calcium-phosphate method. After being cultured, the transfected cells were harvested and used in an immunoblotting process with anti-SIVmac antibodies granted from Dr. Hunsmann at Deutsches Primatenzentrum (DPZ). The immunobots are shown in FIG. 3. In contrast to the plasmid pTV2 used as a control, pTV-SIV/GE and pTV-SIV/pol each expressed a proteins capable of association with an antibody specific for SIV as shown in FIG. 3. Therefore, the plasmids pTV-SIV/GE and pTV-SIV/pol can effectively express SIV proteins in animal cells.

In another aspect of the present invention, there are provided plasmids pHIV/GE and pHIV/pol, in which SIV-derived genes anchored in plasmids pSIV/GE and pSIV/pol are substituted with corresponding genes derived from HIV, respectively.

In more detail, pHIV/GE was prepared by substituting SIV-derived gag, protease, env, and rev genes of pSIV/GE with HIV-derived gag, protease, env and rev genes, respectively. Likewise, the plasmid pHIV/pol carries a HIV-derived pol gene substituting for the SIV-derived pol gene.

Figure 4:
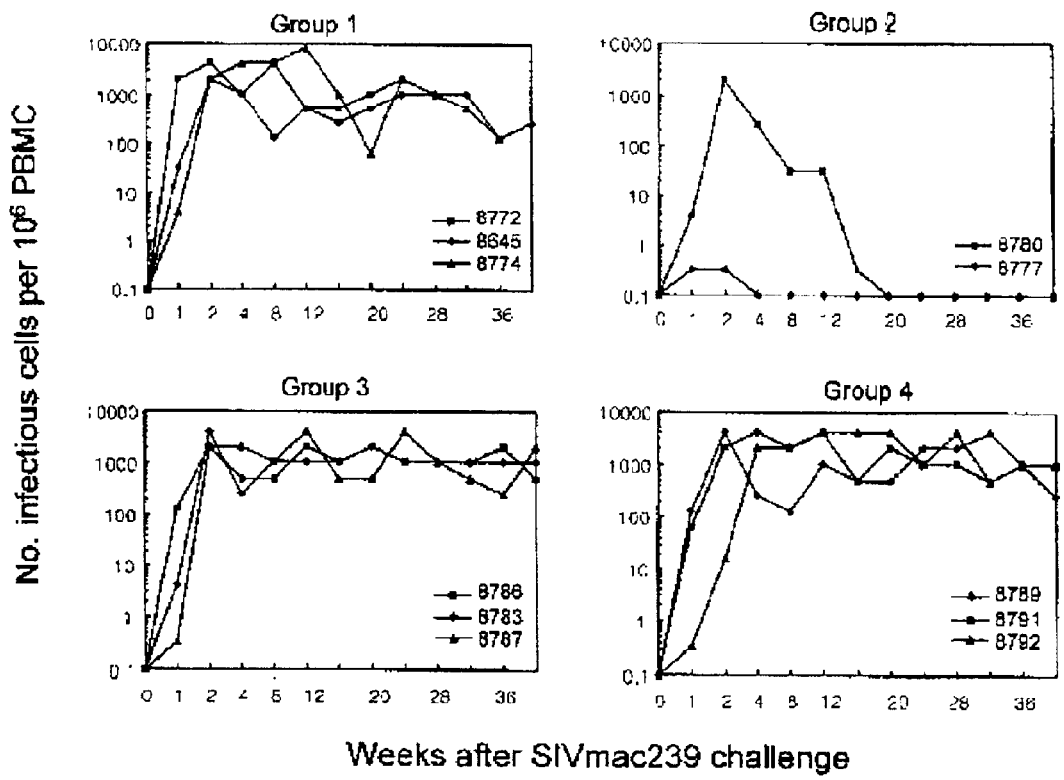

When pTV-SIV/GE and pTV-SIV/pol were injected as a vaccine into rhesus monkeys, the cell associated viral loads in blood (see FIG. 4), the reduction in $CD4^+$ cell count (see FIG. 5), which is typical of AIDS progression, and the drop in the percentage of $CD29^+CD4^+$ cells in PBLs (peripheral blood lymphocytes) (see FIG. 6), which is an early prognostic marker for a decline in immune functions, were all suppressed. Particularly, the infection by SIVmac239 was completely suppressed.

SIVmac/rhesus monkey models are difficult to protect from infection, but recognized as being the closest model to HIV-infected humans (Hanke et al., J. Virol., 73:7524, 1999). It is thus obvious that the plasmids pHIV/GE and pHIV/pol, HIV-substitute types for the plasmids pSIV/GE and pSIV/pol of the present invention, of which pTV-SIV/GE and pSIV/pol are representative, respectively, can be used as DNA vaccines for the prophylaxis and therapy of AIDS.

In a further aspect of the present invention, there are provided DNA vaccines for the prophylaxis and therapy of AIDS caused by SIV or HIV. In detail, vaccines comprising plasmids pSIV/GE and pSIV/pol are useful in the prophylaxis and therapy of the AIDS caused in SIV-infected monkeys. DNA vaccines comprising plasmids pHIV/GE and pHIV/pol as pharmaceutically effective ingredients can be used to prevent and treat AIDS in humans.

In regard to administration routes and manners and formulations, the vaccines of the present invention may follow those of general vaccines, especially DNA vaccines. For example, the DNA vaccines of the present invention may be administered in a general dosage form which uses a parenteral route for its administration.

In the present invention, it is revealed that use of the plasmids pTV-SIV/GE and pTV-SIV/pol as vaccines can protect rhesus monkeys from infection by SIVmac239 (see FIG. 4). In addition, SIV-infected rhesus monkeys administered with the vaccines comprising the plasmid pTV-SIV/GE and pTV-SIV/pol, showed significant suppression in the reduction of $CD4^+$ cell count (see FIG. 5), which is typical of AIDS progression caused by the infection by SIVmac239, and in the reduction of $CD29^+CD4^+$ percentage in total immune cells (see FIG. 6), which indicates deterioration of immune functions. In addition, immunizations of pTV-SIV/GE and pTV-SIV/pol can drop SIVmac induced p27 antigenemia in plasma (FIG. 7), and also generate immune responses to control the viral replication in lymph node (LN) enough to eventually clear the virus (FIG. 8). Since the plasmids pTV-SIV/GE and pTV-SIV/pol are representative examples of the plasmids pSIV/GE and pSIV/pol, plasmid combinations, such as pSIV/GE-pSIV/pol, pHIV/GE-pHIV/pol, can be used as effective ingredients in the DNA vaccines of the present invention.

In the DNA vaccines, the plasmids are contained at a dosage of 0.01–0.1 mg/kg and preferably at a dosage of 0.02–0.05 mg/kg.

A better understanding of the present invention may be obtained in light of the following examples which are set forth to illustrate, but are not to be construed to limit the present invention.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Construction of AIDS DNA Vaccines Useful as SIV Immunogen

Construction of the plasmid pTV-SIV/GE started with the amplification of SIV genes of interest. In this regard, a polymerase chain reaction method was used while a SIVmac239 clone (Regier et al., *AIDS Res. Hum. Retroviruses,* 6:1221–1231, 1990, deposited with GenBank Accession No: M3326) served as a template.

In detail, a PCR product was obtained using as a set of PCR primers synthetic oligonucleotides 1193 Kpn described in the SEQ. ID NO. 1 and 3464Xba described in the SEQ. ID NO. 2, which had restriction sites for KpnI and XbaI, respectively, followed by the partial digestion with Kpn and XbaI. Of the fragmented PCR products, a DNA stretch at base positions 1193–3494 of SIVmac239 was inserted between the restriction sites SalI and XbaI of pBluescript $SK^+$ (Stratagen) to give a recombinant plasmid pSK-SIVgag. Next, a PCR product was prepared using as a set of PCR primers synthetic oligonucleotides 6695Xba described in the SEQ. ID NO. 3 and 9641NotI described in the SEQ. ID NO. 4 which were designed to have restriction sites for XbaI and NotI, respectively. This PCR was double cut with NotI and XbaI and fused with the plasmid pSK-SIVgag which had been partially digested with the same restriction enzymes, so as to give a new recombinant plasmid, pSK-SIV/ge-1.

From the SIVmac239 clone, a DNA fragment was amplified by PCR using synthetic oligonucleotides 8328Cla described in the SEQ. ID NO. 5 and 9535Xho described in the SEQ. ID NO. 6 as a set of primers. After being cut with ClaI and XhoI, the PCR product was inserted into pBluscript $SK^+$ (Stratagene) at the SmaI position to give a new plasmid pSK-SIVenv3.

The two plasmids pSK-SIV/ge-1 and pSK-SIVenv3 were each digested with ClaI and NotI. The vector-containing half of the digested pSK-SIV/ge-1 was fused with the non-vector half of the digested pSK-SIVenv3 to construct the desired plasmid pSK-SIV/GE. A DNA fragment of interest was obtained by cutting the plasmid pSK-SIV/GE with KpnI and NotI and inserted to the KpnI/NotI site of pTV2 (Lee et al., *J. Virol.,* 72:8430, 1998) to give a recombinant plasmid pTV-SIV/GE.

Construction of the plasmid pTV-SIV/pol was conducted as follows. To begin with, a base sequence at positions 3105–5668 of SIVmac239 was amplified by PCR using as a set of PCR primers synthetic oligonucleotides having restriction sites BamHI described in the SEQ. ID NO. 7 and XhoI described in the SEQ. ID NO. 8, respectively, followed by the digestion with restriction enzymes BamHI and XhoI. The plasmid pSK+gDsE2 (Lee et al., *J. Virol.,* 72:8430, 1998) was removed of the E2 portion by use of BglII and XhoI, after which the PCR-amplified BamHI/XhoI fragment was inserted to the truncated PSK-gDsE2 to give a recombinant plasmid pSK+gDSIV/pol. The integrase region of the pol gene was removed of the bases at positions 5130–5132 while the bases at 5133–5135 were mutated so as to express $Ser_{117}$ instead of $Asn_{117}$, to give pSK+gDsSIV/polm.

For the mutation of the pol gene, the plasmid pSK+gDsSIV/pol was used as a PCR template with two synthetic oligonucleotides described in the SEQ. ID NOs. 9 and 10 serving as PCR primers. The PCR product was self-ligated to give the plasmid pSK+gDsSIV/polm. Finally, a DNA fragment of interest, which was obtained by cutting the plasmid pSK+gDsSIV/polm with NotI and XhoI, was inserted to the plasmid pTV2 (Lee et al., *J. Virol.,* 72:8430, 1998) at the same restriction sites.

With the aim of enhancing the immune responses induced by the SIV DNA vaccine, plasmids pTV-SIV/pol-IL-2 and pTV-SIV/GE-GC were constructed which could further express cytokines IL-2 (interleukin-2) and GM-CSF (granulocyte/macrophage-colony stimulating factor), respectively.

In detail, to construct the plasmid pTV-SIV/pol-IL-2, a human IL-2 gene (Chung et al., *I. Hsueh. Tsa. Chih.*, 13:78, 1993) was fused to the IRES (internal ribosomal entry site) sequence of EMCV (Encephalomyocarditis virus), after which the resulting chimeric DNA fragment was inserted into the pTV vector, followed by fusing a SIV gene region of the pSK+gDsSIV/polm to the 5'-end of the IRES. A human GM-CSF gene necessary for the construction of the pTV-SIV/GE-GC was obtained from SupT-1 cell purchased from Korean Cell Line Bank) by RT-PCR using synthetic oligonucleotides described in the SEQ. ID NOs. 11 and 12 as a set of PCR primers. Before the RT-PCR, the cell was activated with Concanavalin A. The obtained human GM-CSF gene was linked to IRES and inserted to the pTV vector, after which the SIV gene was cut out of the pSK-SIV/GE and fused to the 5'-end of the IRES.

DH5α cells were transformed with the plasmids pTV-SIV/GE, pTV-SIV/pol, pTV-SIV/pol-IL-2, and pTV-SIV/GE-GC, respectively and cultured. From the cells, each of the plasmids was prepared by a CsCl-EtBr method. The transformed strains were deposited in the Korean Collection for Type Culture of Korea Research Institute of Bioscience and Biotechnology (KRIBB) on Nov. 27, 1999 (Accession NO: KCTC 0702BP and KCTC 0703BP).

All base sequences used in the construction of the plasmid pTV-SIV/GE and pTV-SIV/pol were numbered on the basis of the base sequence of SIVmac239. All of the gene manipulation processes used above, including use of restriction enzymes, insertion of base sequences, *E. coli* transformation, and plasmid purification, were conducted following the teachings of Sambrook et al. (Molecular Cloning, 2nd Edition, Cold Spring Harbor Laboratory Press, U.S.A., 1989).

Example 2

Immunization of Monkeys with pTV-SIV/GE and pTV-SIV/pol

Each of the plasmids prepared in the Example 1 was dissolved to the concentration of 1 mg/ml in physiological saline (0.85% NaCl). Into two rhesus monkeys (Group 2), the plasmids pTV-SIV/GE and pTV-SIV/pol were administered by intramuscular injection at a dose of 400 μg, each, per head. For a control group (Group 1) comprising three rhesus monkeys, a vector DNA carrying no SIV genes (pTV) was used at a dose of 800 μg in the same injection manner.

Another test group (Group 3) comprising three rhesus monkeys was immunized with pTV-SIV/GE and pTV-SIV/pol, along with the cytokine gene-carrying plasmids pTV-SIV/GE-GC and pTV-SIV/pol-IL-2, each of the four plasmids being used at an amount of 200 ug per head. A final test group (Group 4) comprising three rhesus monkeys was tested for protective immune responses when DNA vaccines and subunit vaccines were used in combination. For the first and the second immunization of this group, a combination of pTV-SIV/GE and pTV-SIV/pol was used. For the third to the fifth immunization, SIVmac-derived p27 proteins (Intracell), gp120 proteins (Intracell) and RT proteins were used at a dose of 50 ug per head, along with alum as an adjuvant. For use in this experiment, the recombinant RT protein was obtained by cloning the RT gene of SIVmac239 in a pRSET vector, expressing the RT in an *E. coli* BL2 strain and purifying it through affinity chromatography using a metal-affinity resin (Pharmacia).

At the 8th, the 17th, the 25th and the 44th weeks after the first immunization, the same immunogens as used in the first immunization were injected into the identical rhesus monkeys in the same manners. The identification and composition of each DNA vaccine was shown in FIG. 9, and the immunization schedule of each group of monkeys was illustrated in FIG. 10.

Example 3

Infection of Immunized Monkeys with SIVmac239

A couple of weeks after the final immunization (i.e., the 46th week after the first immunization), SIVmac239 (Deutsches Primatensentrum, injection volume 1 ml) was injected intravenously at a dose ten times as large as a predetermined $MID_{50}$ (monkey infectious dose) into each of the immunized rhesus monkeys.

Experimental Example 1

Measurement of SIV Infected Cells in PBMC After the SIVmac Challenge

To know to what extent the immunity induced by the plasmids allows the monkeys to be resistant to SIV, that is, whether the rhesus monkeys have sterilizing immunity to kill the viruses, or whether the immune responses induced in the rhesus monkeys are potent enough to control the viral replication although not to kill the viruses, the peripheral blood mononuclear cells (PBMC) infected by SIV were measured.

At 1, 2, 4, 8, 12, 16, 20, 24, 28, 32, 36 and 40 weeks after the SIVmac239 infection, PBMC were isolated from control and test rhesus monkeys. A measurement was made of the number of SIV-infected PBMC per one million cells according to the limiting-dilution cocultivation method (Lu et al., *J. Virol.,* 70:3978, 1996).

The results of the examination on immune induction effects of the plasmids are given in FIG. 4. In the control group which was immunized with pTV, the number of the SIV-infected PBMC was sharply increased at the 1st and the 2nd weeks after the infection with SIVmac239 and thereafter, maintained at a level of 100–10,000 per one million cells.

On the quite contrary, one of the two rhesus monkeys immunized with a combination of pTV-SIV/GE and pTV-SIV/pol according to the present invention was found to maintain very low infected PBMC counts until the 2nd week after the infection, and be free of virus-infected cells from the 4th week. This result indicates that the immune system of the immunized rhesus monkey effectively clear SIVmac239, thereby perfectly protecting the monkey from infection.

In the other immunized rhesus monkey, a maximum level of SIV-infected PBMC were counted at the 4th week after the infection, but after that, the SIV-infected PBMC count decreased gradually and no infected cells were detected at the 20th week and thereafter, which demonstrates that the immune system of this monkey well functions to control the replication of the virus.

Like the control group, no rhesus monkeys of the test group (group 3) immunized with the DNA vaccines carrying cytokine genes showed inhibition of the viral replication. To our knowledge, the accessory cytokine genes, administered together with the necessary genes, activate immune responses in a direction advantageous to the replication of the viruses.

Rhesus monkeys of the test group (group 4) which was immunized with SIV DNA, followed by boosting with subunit vaccines, do not significantly differ from those of the control groups in SIV-infected PBMC count patterns. In consequence, the subunit proteins can be deduced to be inferior to the DNA vaccines themselves in boosting effect or to convert the induced immune responses toward a direction advantageous to the infection of viruses.

Experimental Example 2

Measurement of Absolute CD4$^+$ Cell Count in Blood

Generally accepted as an indicator useful in determining the progression of AIDS is an absolute CD4$^+$ cell count in blood. At the 1st, the 2nd, the 4th, the 6th, the 8th, the 12th, the 16th, the 20th, the 24th and the 28th weeks after the SIVmac infection, CD4$^+$ cells in PBL (peripheral blood lymphocytes) were counted by use of a FACS (fluorescent automated cell sorter), such as that manufactured by Becton-Dickinson, identified as FACScan (Bjorn et al., *J. Virol.*, 72:7846, 1998).

Figure 5:
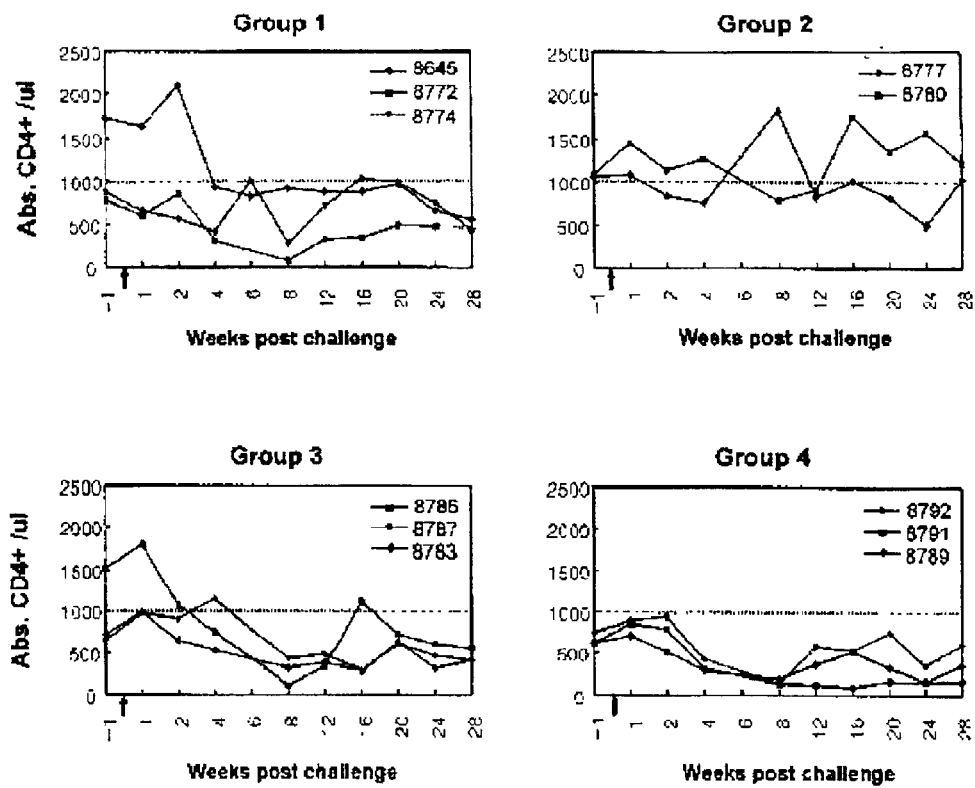

FACS results are given in FIG. 5. For the control group immunized with pTV, the rhesus monkeys suffered from the reduction of CD4$^+$ cell at the 1st, the 2nd and the 4th weeks after the SIVmac239 infection. At the 28th week, the CD4$^+$ cell count was much lower as compared with that at the last week before the challenge.

In contrast, the rhesus monkeys immunized with the plasmids of the present invention were found to have average CD4$^+$ cell counts higher than those of the control group during the observation period, and retain as many CD4$^-$ cells on average at the 28th week as before infection, indicating that immunization by the plasmids of the present invention effectively inhibited the reduction of absolute CD4$^+$ cell count caused by SIVmac239 infection.

Like the control group, both the test group immunized with cytokine gene-carrying plasmids and the test group immunized with plasmids and boosted with subunit vaccines, suffered from the decrease in CD4$^+$ cells.

Experimental Example 3

Measurement of CD29$^+$CD4$^+$ Percentage in Blood

The percentage of CD29$^+$CD4$^+$ cell in total immune cells is known as an early predictor for determining whether immune functions are deteriorated in humans and monkeys (Blatt et al., *J. Infect Dis.*, 171:837, 1995; Kneitz et al, *Vet Immunol. Immunopathol.*, 36:239, 1993). At the 1st, the 2nd, the 4th, the 6th, the 8th, the 12th, the 16th, the 20th, the 24th and the 28th weeks after the SIVmac infection, blood samples taken from the immunized rhesus monkeys were measured for percentages of CD29$^+$CD4$^+$ cell in PBL with the aid of FACS (Bjorn et al., *J. Virol.*, 72:7846, 1998).

Figure 6:
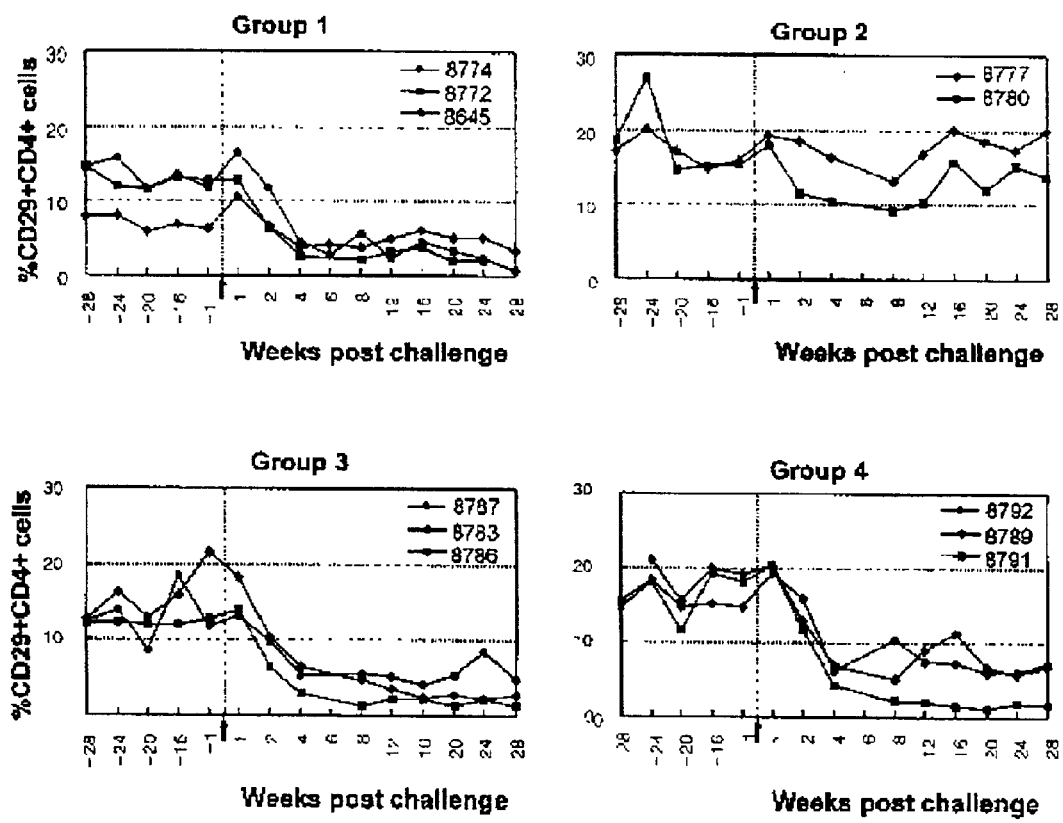

The FACS results are given in FIG. 6. In the control group immunized with pTV, the percentage of CD29$^+$CD4$^+$ cell continued to decrease until the 4th week after the SIVmac239 infection and were measured to be below 5% of total PBL at the 28th week.

The rhesus monkeys immunized with the plasmids of the present invention showed average percentages of CD29$^+$CD4$^+$ cell higher than those of the control group at each measurement time and maintained the percentages of CD29$^+$CD4$^+$ cell at about 10–20%, which is the level found in normal monkeys, at the 28th week. This result demonstrates that the immunity induced by the plasmids of the present invention effectively inhibits the reduction of CD29$^+$CD4$^+$ percentage caused by SIVmac239, that is, the deterioration of immune function, corresponding to the results of Experimental Examples 1 and 2.

In both the test group immunized with cytokine gene-carrying plasmids and the test group immunized with plasmids and boosted with subunit vaccines, the percentage of CD29$^+$CD4$^+$ cell in the total immune cells were measured to be decreased, like in the control group.

Experimental Example 4

Figure 7:
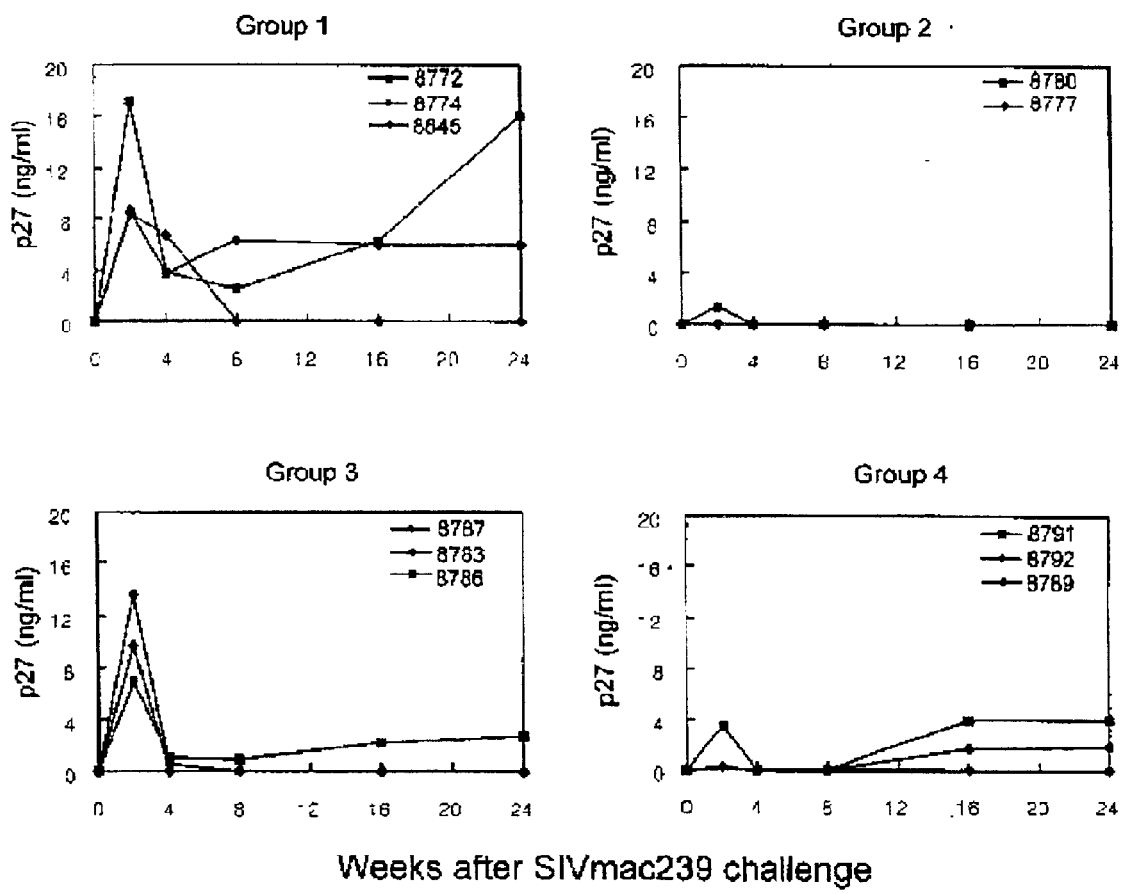
Figure 10:
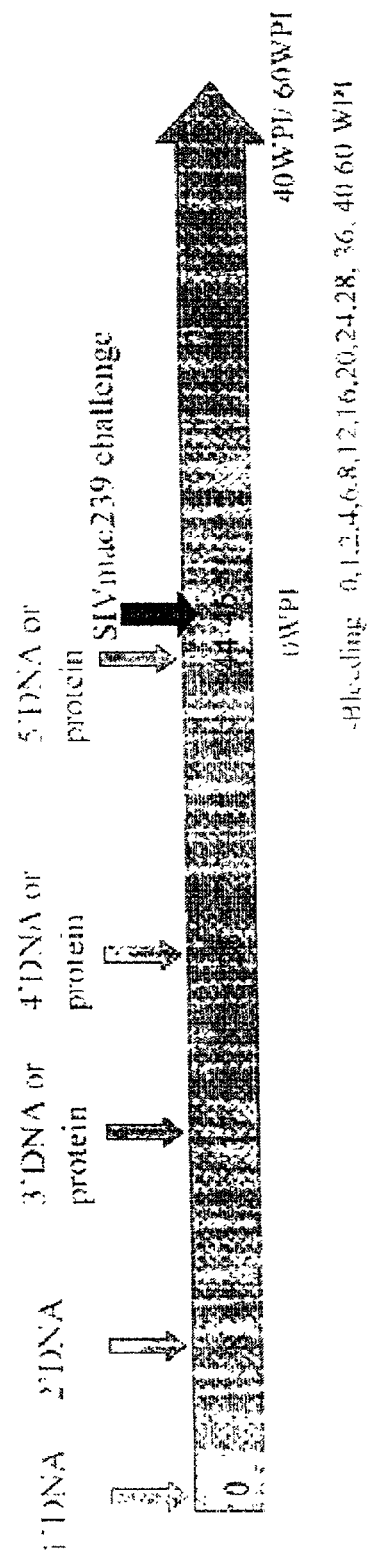

Measurement of the Postchallenge Level of the p27 Antigenemia in Plasma of Immunized Monkeys The challenged animals were tested for p27 antigenemia at 0, 2, 4, 8, 16, 24 weeks postchallenge (FIG. 7). Levels of antigenemia were determined by analysis of plasma by p27 antigen capture ELISA.

As a result, the levels of p27 in plasma of SIV DNA-vaccinated animals were less than those of control DNA vaccinated monkeys during the observation period. In particular, the serum p27 levels of two monkeys immunized with pTV-SIV/GE plus pTV-SIV/pol were shown to be much lower or undetectable in comparison with those of monkeys immunized with other AIDS vaccines. This result is consistent with cell associated viral loads in blood, and indicates that immune responses generated by immunization with pTV-SIV/GE and pTV-SIV/pol can inhibit the viral replication in blood of immunized monkeys.

Experimental Example 5

Measurement of the Cell Associated Viral Load in Lymph Node of Immunized Monkey After the SIVmac Challenge Inguinal lymph node (LN) biopsies were collected at 25 weeks post challenge for 8777, 8780 monkey in Group 2. Additional axillary LN specimens were collected at 52 weeks post challenge for 8777, 8780 monkey in Group 2 and for 8783 monkey in Group 3. At 60 weeks post infection, cervical LN, palatine tonsil, lingual tonsil, spleen, axillary LN, mesenteric LN, submandibular LN, thymus, retropharyngeal LN and Peyer's patches biopsies were collected for 8777, 8780 monkey.

Consistent with cell associated viral loads in blood, the viral loads in lymph nodes of the DNA immunized monkeys (Group 2) were very low or undetectable. As shown in FIG. 8, the number of SIVmac-infected cells per $10^6$ mononuclear cells in axillary lymph nodes of Group 2 was only 1 (#8780)

or undetectable (#8777), while one monkey (#8783) of Group 3 had 1024 infected cells per $10^6$ mononuclear cells at 52 WPI. In addition, all monkeys of Group 2 had no detection of SIV-infected cells in axillary lymph node at 60 WPI. This result suggests that immune responses generated by DNA immunization with pTV-SIV/GE and pTV-SIV/pol also control viral replication enough to eventually clear the virus in lymph nodes.

INDUSTRIAL APPLICABILITY

The present invention provides DNA vaccines which are capable of perfectly preventing the infection by SIVmac virus and preventing the deteriotion of immune functions caused by SIVmac virus, as described above and proven in SIVmac/rhesus monkey models, which are the most ideal for developing AIDS DNA vaccines and the most difficult to protect. The AIDS DNA vaccines of the present invention are found to be far better in efficacy and safety than any other AIDS vaccines known thus far. Of the DNA vaccines of the present invention, plasmids carrying HIV genes instead of corresponding SIV genes are predicted to have similar medicinal potency on humans. With the capability of inhibiting the replication of AIDS viruses and completely eliminating them in blood and lymph nodes, the DNA vaccines are suitable for use not only as preventive agents against infection by AIDS viruses, but also as therapeutic agents eradicative of surviving AIDS viruses when used in combination with other curative agents. Consequently, the present invention offers AIDS DNA vaccines which successfully exert perfect medicinal efficacy on primates, giving a measure of success in developing effective AIDS DNA vaccines applicable to humans.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A DNA vaccine for prevention of AIDS in rhesus monkeys comprising:

a first plasmid, pTV-SIV/GE (Accession NO: KCTC 0702BP), and a second plasmid, pTV-SIV/pol (Acession NO: KCTC 0703BP), wherein said DNA vaccine lacks genes encoding IL-2 and GM-CSF.

* * * * *